(12) United States Patent
Smyth et al.

(10) Patent No.: US 9,370,514 B2
(45) Date of Patent: Jun. 21, 2016

(54) METHODS FOR FINE PARTICLE MANUFACTURE

(71) Applicant: Board of Regents, The University of Texas System, Austin, TX (US)

(72) Inventors: Hugh D. C. Smyth, Austin, TX (US); Matt Herpin, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/458,818

(22) Filed: Aug. 13, 2014

(65) Prior Publication Data

US 2015/0050345 A1    Feb. 19, 2015

Related U.S. Application Data

(60) Provisional application No. 61/865,782, filed on Aug. 14, 2013.

(51) Int. Cl.
*A61K 31/496*     (2006.01)
*A61K 9/14*       (2006.01)
*A61K 31/192*     (2006.01)

(52) U.S. Cl.
CPC .............. *A61K 31/496* (2013.01); *A61K 9/14* (2013.01); *A61K 9/145* (2013.01); *A61K 31/192* (2013.01)

(58) Field of Classification Search
None
See application file for complete search history.

(56) References Cited

U.S. PATENT DOCUMENTS

| | | | |
|---|---|---|---|
| 5,700,471 A | 12/1997 | End et al. | |
| 5,785,976 A | 7/1998 | Westesen et al. | |
| 6,682,761 B2 | 1/2004 | Pace et al. | |
| 2002/0012704 A1* | 1/2002 | Pace ...................... | A61K 9/145 424/489 |
| 2003/0059472 A1 | 3/2003 | Brynjelsen et al. | |
| 2009/0214645 A1 | 8/2009 | Kramer et al. | |

FOREIGN PATENT DOCUMENTS

WO    01/80828    11/2001

OTHER PUBLICATIONS

International Search Report and Written Opinion issued in International Application No. PCT/US2014/050923, dated Oct. 21, 2014, 13 pages.

* cited by examiner

*Primary Examiner* — Robert A Wax
*Assistant Examiner* — Melissa Mercier
(74) *Attorney, Agent, or Firm* — Meunier Carlin & Curfman LLC (57) ABSTRACT

Processes for preparing micronized particles comprising a poorly water soluble bioactive agent are provided. The processes utilize a superheated aqueous phase which can serve as the continuous phase of an emulsion. The superheated aqueous phase can be used to melt poorly water soluble bioactive agents and/or matrix materials which them form molten droplets dispersed within the superheated aqueous phase. The size and size distribution of the molten droplets can be controlled using a variety of suitable methods. The molten droplets can then be cooled to form micronized particles comprising the poorly water soluble bioactive agent. If desired, the cooling rate can be selected to control the crystalline morphology of the resulting micronized particles.

20 Claims, 3 Drawing Sheets

METHODS FOR FINE PARTICLE MANUFACTURE

CROSS-REFERENCE TO RELATED APPLICATIONS

This application claims benefit of U.S. Provisional Application No. 61/865,782, filed Aug. 14, 2013, the disclosure of which is expressly incorporated herein by reference.

BACKGROUND

Recent advances in molecular biology have provided a vast array of potential new bioactive agents. However, it has been estimated that 60% of new bioactive agents exhibit limited water solubility. Formulating poorly water soluble bioactive agents into suitable dosage forms poses a significant challenge due to difficulties in achieving adequate bioavailability of the bioactive agent in an aqueous biological system.

In principle, the bioavailability of poorly water-soluble bioactive agents can be improved by decreasing the particle size of the bioactive agent. Various methods of reducing particle size have been explored, including milling, high pressure homogenization, spray drying, lyophilization of solutions in water-organic solvent mixtures, and lyophilization of solutions in organic solvents. However, existing approaches for micronizing poorly water-soluble drugs have significant drawbacks. For example, many conventional approaches fail to provide precise control of particle size and/or particle size distribution. Other methods require the use of organic solvents that can remain in the comminuted product. Improved methods of preparing micronized particles are needed to provide pharmaceutical formulations of poorly water soluble bioactive agents which can be readily prepared and which can improve the bioavailability of the poorly water soluble bioactive agent.

SUMMARY

Processes for preparing micronized particles comprising a poorly water soluble bioactive agent are provided. Processes for preparing micronized particles comprising a poorly water soluble bioactive agent can comprise (a) heating an aqueous suspension comprising the poorly water soluble bioactive agent to a temperature of from about 100° C. to about 280° C. at a pressure of from greater than standard pressure to about 1,000 psi to form a superheated continuous phase comprising molten droplets of the poorly water soluble bioactive agent dispersed in superheated water; and (b) cooling the molten droplets to form micronized particles comprising the poorly water soluble bioactive agent. Processes can further comprise reducing the size of the molten droplets while maintaining the superheated continuous phase at a temperature of from about 100° C. to about 280° C. and a pressure of from greater than standard pressure to about 1,000 psi.

Also provided are processes for preparing micronized particles comprising a poorly water soluble bioactive agent which comprise (a) melting the poorly water soluble bioactive agent, (b) introducing the melted poorly water soluble bioactive agent into a superheated aqueous phase heated to a temperature of from about 100° C. to about 280° C. at a pressure of from greater than standard pressure to about 1,000 PSI to form a superheated continuous phase comprising molten droplets of the poorly water soluble bioactive agent dispersed in superheated water, and (c) cooling the molten droplets to form micronized particles comprising the poorly water soluble bioactive agent. In certain embodiments, step (b) comprises a superheated aqueous phase heated to a temperature ranging from the melting point of the poorly water soluble bioactive agent to 20° C. higher than the melting point of the poorly water soluble bioactive agent (e.g., heated to a temperature ranging from the melting point of the poorly water soluble bioactive agent to 10° C. higher than the melting point of the poorly water soluble bioactive agent).

Introducing the melted poorly water soluble bioactive agent into the superheated aqueous phase can comprise injecting droplets of the melted poorly water soluble bioactive agent into the superheated aqueous phase. Injecting droplets of the melted poorly water soluble bioactive agent into the superheated aqueous phase can comprise spraying the melted poorly water soluble bioactive agent into the superheated aqueous phase. Injecting droplets of the melted poorly water soluble bioactive agent into the superheated aqueous phase can comprise extruding the melted poorly water soluble bioactive agent into the superheated aqueous phase. For example, the melted poorly water soluble bioactive agent can be extruded into the superheated aqueous phase through a microporous membrane (i.e., membrane emulsification). In certain embodiments, the superheated aqueous phase is flowing orthogonally to the surface of the microporous membrane during extrusion of the melted poorly water soluble bioactive agent into the superheated aqueous phase (i.e., cross-flow membrane emulsification).

In variations of the processes described above, a matrix material and a poorly water soluble bioactive agent are added to the aqueous phase. These processes can be used to form micronized particles comprising a mixture of a matrix material and a poorly water soluble bioactive agent. Thus, also provided are processes for preparing micronized particles comprising a poorly water soluble bioactive agent that can comprise (a) heating an aqueous suspension comprising a matrix material and the poorly water soluble bioactive agent to a temperature of from about 100° C. to about 280° C. at a pressure of from greater than standard pressure to about 1,000 PSI to form a superheated continuous phase comprising molten droplets of the matrix material dispersed in superheated water, and (b) cooling the molten droplets to form micronized particles comprising the matrix material and the poorly water soluble bioactive agent. In certain embodiments, step (a) comprises heating the aqueous suspension to a temperature ranging from the melting point of the matrix material to 10° C. higher than the melting point of the matrix material.

Any suitable matrix material can be used. The matrix material can be, for example, a polymer, wax, or lipid which provides for the controlled release of the poorly water soluble bioactive agent. The poorly water soluble bioactive agent can have a higher melting point than the matrix material. The aqueous suspension can be heated to a temperature greater than the melting point of both the matrix material and the poorly water soluble bioactive agent. Alternatively, the aqueous suspension can be heated to a temperature ranging from the melting point of the matrix material to less than the melting point of the poorly water soluble bioactive agent. In these embodiments, molten droplets of the matrix material can serve as a solvent in which the poorly water soluble bioactive agent is dissolved or dispersed. In certain cases, the poorly water soluble bioactive agent dissolves in the molten droplets of the matrix material, and step (b) comprises cooling the molten droplets to form micronized particles comprising the first poorly water soluble bioactive agent and the second poorly water soluble bioactive agent. In other cases, the poorly water soluble bioactive agent becomes dispersed in the molten droplets of the matrix material, and step (b) comprises cooling the molten droplets to form micronized particles comprising the first poorly water soluble bioactive agent and the second poorly water soluble bioactive agent.

Also provided are micronized particles formed using the processes described herein, as well as pharmaceutical formulations which include the micronized particles.

DETAILED DESCRIPTION

Processes for preparing micronized particles comprising a poorly water soluble bioactive agent are provided. The processes utilize a superheated aqueous phase (i.e., an aqueous liquid under pressure at a temperature ranging from the aqueous liquid's boiling point to the aqueous liquid's critical temperature, such as liquid water under pressure at a temperature ranging from about 100° C. to about 374° C.) which can serve as the continuous phase of an emulsion. The superheated aqueous phase can be used to melt poorly water soluble bioactive agents and/or matrix materials which them form molten droplets dispersed within the superheated aqueous phase. The size and size distribution of the molten droplets can be controlled using a variety of suitable methods. The molten droplets can then be cooled to form micronized particles comprising the poorly water soluble bioactive agent. If desired, the cooling rate can be selected to control the crystalline morphology of the resulting micronized particles.

Processes for preparing micronized particles comprising a poorly water soluble bioactive agent can comprise (a) heating an aqueous suspension comprising the poorly water soluble bioactive agent to a temperature of from about 100° C. to about 280° C. at a pressure of from greater than standard pressure to about 1,000 psi to form a superheated continuous phase comprising molten droplets of the poorly water soluble bioactive agent dispersed in superheated water; and (b) cooling the molten droplets to form micronized particles comprising the poorly water soluble bioactive agent. Processes can further comprise reducing the size of the molten droplets while maintaining the superheated continuous phase at a temperature of from about 100° C. to about 280° C. and a pressure of from greater than standard pressure to about 1,000 psi.

The temperature to which the aqueous suspension is heated can be selected in view of a number of factors, including the identity of the poorly water soluble bioactive agent (e.g., the melting point of the poorly water soluble bioactive agent, the thermal stability of the poorly water soluble bioactive agent, etc.), processing parameters such as the method of reducing the size of the molten droplets, the desired average particle size of the resulting micronized particles, the desired particle size distribution of the resulting micronized particles.

The aqueous suspension in step (a) can be heated to a temperature of at least about 100° C. (e.g., at least about 110° C., at least about 120° C., at least about 130° C., at least about 140° C., at least about 150° C., at least about 160° C., at least about 170° C., at least about 180° C., at least about 190° C., at least about 200° C., at least about 210° C., at least about 220° C., at least about 230° C., at least about 240° C., at least about 250° C., at least about 260° C., or at least about 270° C.). In some embodiments, the aqueous suspension can be heated to a temperature about 280° C. or less (e.g., about 270° C. or less, about 260° C. or less, about 250° C. or less, about 240° C. or less, about 230° C. or less, about 220° C. or less, about 210° C. or less, about 200° C. or less, about 190° C. or less, about 180° C. or less, about 170° C. or less, about 160° C. or less, about 150° C. or less, about 140° C. or less, about 130° C. or less, about 120° C. or less, or about 110° C. or less).

The aqueous suspension in step (a) can be heated to a temperature ranging from any of the minimum temperatures described above to any of the maximum temperatures described above. For example, the aqueous suspension in step (a) can be heated to a temperature ranging from about 100° C. to about 280° C. (e.g., from about 100° C. to about 245° C., from about 100° C. to about 200° C., or from about 150° C. to about 250° C.).

In certain embodiments, the temperature to which the aqueous suspension is heated can be selected in view of the identity of the poorly water soluble bioactive agent, processing parameters such as the method of reducing the size of the molten droplets, the desired average particle size of the resulting micronized particles, the desired particle size distribution of the resulting micronized particles. As the aqueous suspension is heated above the melting point of the poorly water soluble bioactive agent, both the viscosity of the molten poorly water soluble bioactive agent and the surface tension of the aqueous phase are decreased. As a result, the size of the molten droplets (and thus the size of the resultant micronized particles) can be more readily reduced in size (i.e., less energy can be introduced to reduce the size of the molten droplets). The aqueous suspension in step (a) can be heated to a temperature greater than the melting point of the poorly water soluble bioactive agent (e.g., at least about 5° C., at least about 10° C., at least about 15° C., at least about 20° C., at least about 25° C., at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., or at least about 95° C. higher than the melting point of the poorly water soluble bioactive agent). The aqueous suspension in step (a) can be heated to a temperature of about 100° C. or less above the melting point of the poorly water soluble bioactive agent (e.g. about 95° C. or less, about 90° C. or less, about 85° C. or less, about 80° C. or less, about 75° C. or less, about 70° C. or less, about 65° C. or less, about 60° C. or less, about 55° C. or less, about 50° C. or less, about 45° C. or less, about 40° C. or less, about 35° C. or less, about 30° C. or less, about 25° C. or less, about 20° C. or less, about 15° C. or less, about 10° C. or less, or about 5° C. or less above the melting point of the poorly water soluble bioactive agent).

The temperature to which the aqueous suspension is heated can range from any of the minimum temperatures described above to any of the maximum temperatures described above. For example, the temperature to which the aqueous suspension is heated can range from the melting point of the poorly water soluble bioactive agent to about 100° C. higher than the melting point of the poorly water soluble bioactive agent (e.g., from about 5° C. higher the melting point of the poorly water soluble bioactive agent to about 100° C. higher than the melting point of the poorly water soluble bioactive agent, from about 5° C. higher the melting point of the poorly water soluble bioactive agent to about 50° C. higher than the melting point of the poorly water soluble bioactive agent, or from the melting point of the poorly water soluble bioactive agent to about 10° C. higher than the melting point of the poorly water soluble bioactive agent).

The aqueous suspension can be heated under a pressure greater than standard pressure (i.e., about 14.7 psi). During heating, the aqueous suspension can be contained in a closed vessel or apparatus at a pressure higher than ambient pressure. The aqueous suspension can be contained in a pressurized closed system such as a stainless steel vessel or bomb which is configured to permit heating of the suspension and optionally reduction of the size of the molten droplets in the superheated continuous phase. The vessel can also be connected through suitable piping and valves to an apparatus to reduce the size of the molten droplets in the superheated continuous phase. The aqueous suspension can be heated under a pressure of at least about 25 psi, at least about 50 psi, at least about 75 psi, at least about 100 psi, at least about 200 psi, at least about 250 psi, at least about 300 psi, at least about 400 psi, at least about 500 psi, at least about 600 psi, at least about 700 psi, at least about 750 psi, at least about 800 psi, or at least about 900 psi. The aqueous suspension can be heated under a pressure of about 1000 psi or less (e.g., about 900 psi or less, about 800 psi or less, about 750 psi or less, about 700 psi or less, about 600 psi or less, about 500 psi or less, about 400 psi or less, about 300 psi or less, about 250 psi or less, about 200 psi or less, about 100 psi or less, about 75 psi or less, about 50 psi or less, or about 25 psi or less).

The aqueous suspension can be heated under a pressure ranging from any of the minimum pressures described above to any of the maximum pressured described above. For example, the aqueous suspension can be heated under a pressure ranging from greater than standard pressure to about 1000 psi (e.g., from greater than standard pressure to about 500 psi, or from about 50 psi to about 500 psi).

The poorly water soluble bioactive agent can be any physiologically or pharmacologically active substances that acts locally or systemically in the body. The bioactive agent can be a substance used for the treatment (e.g., a therapeutic agent), prevention (e.g., a prophylactic agent), diagnosis (e.g., a diagnostic agent), cure or mitigation of disease or illness, a substance which affects the structure or function of the body (e.g., a nutritional agent), or a pro-drug which becomes biologically active or more active after they have been placed in a predetermined physiological environment. Examples of suitable bioactive agents include anti-neoplastic agents, anthelmintics agents, antibiotics, anticoagulants, antidepressants, antidiabetic agents, antiepileptics, antihistamines, antihypertensive agents, antimuscarinic agents, antimycobacterial agents, immunosuppressants, antithyroid agents, antiviral agents, anxiolytic sedatives, astringents, beta-adrenoceptor blocking agents, beta-adrenergic agonists, cardiac inotropic agents, contrast media, corticosteroids, cough suppressants, diagnostic agents, diagnostic imaging agents, diuretics, dopaminergics, haemostatics, immunological agents, lipid regulating agents, muscle relaxants, parasympathomimetics, parathyroid calcitonin, biphosphonates, protease inhibitors, prostaglandins, radiopharmaceuticals, sex hormones, steroids, anti-allergic agents, stimulants, sympathomimetics, thyroid agents, vasodilators and xanthines, disulfide compounds, antibacterials, antivirals, nonsteroidal anti-inflammatory drugs, analgesics, anticoagulants, anticonvulsants, antiemetics, antifungals, anti-inflammatory agents, antiprotozoals, antipsychotics, cardioprotective agents, cytoprotective agents, antiarrhythmics, hormones, immunostimulating agents, lipid-lowering agents, platelet aggregation inhibitors, agents for treating prostatic hyperplasia, agents for treatment of rheumatic disease, vascular agents, nutrients, vitamins, imaging agents, contrast agents, and combinations thereof. A detailed description of these and other suitable bioactive agents may be found in Remington's Pharmaceutical Sciences, 18th edition, 1990, Mack Publishing Co. Philadelphia, Pa. which is hereby incorporated by reference.

The poorly water soluble bioactive agent can have a solubility in water at 25° C. of about 10.0 mg/mL or less (e.g., about 9.5 mg/mL or less, about 9.0 mg/mL or less, about 8.5 mg/mL or less, about 8.0 mg/mL or less, about 7.5 mg/mL or less, about 7.0 mg/mL or less, about 6.5 mg/mL or less, about 6.0 mg/mL or less, about 5.5 mg/mL or less, about 5.0 mg/mL or less, about 4.5 mg/mL or less, about 4.0 mg/mL or less, about 3.5 mg/mL or less, about 3.0 mg/mL or less, about 2.5 mg/mL or less, about 2.0 mg/mL or less, about 1.5 mg/mL or less, about 1.0 mg/mL or less, about 0.75 mg/mL or less, about 0.50 mg/mL or less, about 0.25 mg/mL or less, about 0.10 mg/mL or less, or less). In some cases, the bioactive agent is substantially insoluble in water (i.e., the bioactive agent has a solubility in water at 25° C. of less than 0.05 mg/mL).

In some embodiments, the poorly water soluble bioactive agent can exhibit a solubility described above in water at physiological pH (i.e., a pH ranging from 6.5 to 7.4). In other embodiments, the poorly water soluble bioactive agent comprises a bioactive agent which exhibits pH-dependent solubility. For example, the poorly water soluble bioactive agent can be a bioactive agent which exhibit a solubility higher than 10.0 mg/mL in water at 25° C. and at physiological pH, but exhibits a solubility described above in water at 25° C. and at a pH lower or higher than physiological pH. In these embodiments, the pH of the aqueous phase can be adjusted by addition of a pH modifier (e.g., an acid or base), such that the bioactive agent exhibits a solubility described above in the aqueous phase during the course of the processes described herein.

In some embodiments, the poorly water soluble bioactive agent can be an amphiphilic bioactive agent. Amphiphilic compounds are molecules which possess both a hydrophilic and a hydrophobic moiety. For example, ibuprofen is amphiphilic when ionized. In these embodiments, the pH of the aqueous phase can be adjusted by addition of a pH modifier (e.g., an acid or base) to ionize at least a portion of the bioactive agent, such that the bioactive agent is amphiphilic. When present, the amphiphilic active agent can reduce the interfacial tension between the aqueous phase and the molten droplets, stabilizing the dispersion.

The poorly water soluble bioactive agent can be an agent can be a bioactive agent which melts without decomposition. In some embodiments, the poorly water soluble bioactive agent can have a melting point of at least about 25° C. (e.g., at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 95° C., at least about 100° C., at least about 105° C., at least about 110° C., at least about 115° C., at least about 120° C., at least about 125° C., at least about 130° C., at least about 135° C., at least about 140° C., at least about 145° C., at least about 150° C., at least about 155° C., at least about 160° C., at least about 165° C., at least about 170° C., at least about 175° C., at least about 180° C., at least about 185° C., at least about 190° C., at least about 195° C., at least about 200° C., at least about 205° C., at least about 210° C., at least about 215° C., at least about 220° C., at least about 225° C., at least about 230° C., at least about 235° C., at least about 240° C., at least about 245° C., at least about 250° C., at least about 255° C., at least about 260° C., at least about 265° C., at least about 270° C., or at least about 275° C.). In some embodiments, the poorly water soluble bioactive agent can have a melting point of about 280° C. or less (e.g., about 275° C. or less, about 270° C. or less, about 265° C. or less, about 260° C. or less, about 255° C. or less, about 250° C. or less, about 245° C. or less, about 240° C. or less, about 235° C. or less, about 230° C. or less, about 225° C. or less, about 220° C. or less, about 215° C. or less, about 210° C. or less, about 205° C. or less, about 200° C. or less, about 195° C. or less, about 190° C. or less, about 185° C. or less, about 180° C. or less, about 175° C. or less, about 170° C. or less, about 165° C. or less, about 160° C. or less, about 155° C. or less, about 150° C. or less, about 145° C. or less, about 140° C. or less, about 135° C. or less, about 130° C. or less, about 125° C. or less, about 120° C. or less, about 115° C. or less, about 110° C. or less, about 105° C. or less, about 100° C. or less, about 95° C. or less, about 90° C. or less, about 85° C. or less, about 80° C. or less, about 75° C. or less, about 70° C. or less, about 65° C. or less, about 60° C. or less, about 55° C. or less, about 50° C. or less, about 45° C. or less, about 40° C. or less, about 35° C. or less, or about 30° C. or less).

The poorly water soluble bioactive agent can have a melting point ranging from any of the minimum values described above to any of the maximum values described above. For example, the poorly water soluble bioactive agent can have a melting point ranging from about 25° C. to about 280° C. (e.g., from about 50° C. to about 280° C., or from about 100° C. to about 280° C.).

Examples of poorly water soluble bioactive agents include albendazole (m.p. 208-210° C.), albendazole sulfoxide, alfaxalone (m.p. 172-174° C.), acetyl digoxin, acyclovir analogs melting at or below 280° C., alprostadil, aminofostin, anipamil, antithrombin III, atenolol (m.p. 146-148° C.), azidothymidine, bacitracin zinc, beclobrate (m.p. 200-204° C.), beclomethasone (m.p. 117-120° C.), belomycin, benzocaine (m.p. 88-90° C.) and derivatives, beta carotene (m.p. 183° C.), beta endorphin, beta interferon, betaxolol HCl, bezafibrate (m.p. 186° C.), binovum, biperiden (m.p. 112-116° C.), brimonidine tartrate, brinzolamide, bromazepam (m.p. 237-238° C.), bromfenac, bromocryptine, bucindolol, buflomedil (m.p. 192-193° C.), bupivacaine (m.p. 107-108° C.), busulfan (m.p. 114-118° C.), cadralazine (m.p. 160-162° C.), camptothesin (m.p. 264-267 and 275° C.), canthaxanthin (m.p. 217° C.), captopril (m.p. 103-104° C.), carbamazepine (m.p. 190-193° C.), carboprost, carvedilol (m.p. 115° C.), cefalexin, cefalotin, cefamandole (m.p. 190° C.), cefazedone, cefluoroxime, cefinenoxime, cefoperazone (m.p. 169-171° C.), cefotaxime, cefoxitin (m.p. 149-150° C.), cefsulodin (m.p. 175° C.), ceftizoxime, chlorambucil (m.p. 64-66° C.), chloramphenicol, chromoglycinic acid, ciclonicate (m.p. 127-128° C.), ciglitazone, ciprofloxacin, clonidine (m.p. 130° C.), cortexolone, corticosterone (m.p. 180-182° C.), cortisol (m.p. 212-220° C.), cortisone (m.p. 220-224° C.), cyclophosphamide (m.p. 41-45° C.), cyclosporins, such as cyclosporin A (m.p. 148-151° C.), cytarabine (m.p. 212-213° C.), desocryptin, desogestrel (m.p. 109-110° C.), dexamethasone, as well as dexamethasone esters such as the acetate ester (m.p. 238-240° C.), dezocine, diazepam (m.p. 125-126° C.), diclofenac, dideoxyadenosine (m.p. 160-163° C.), dideoxyinosine, difluprednate, digitoxin (m.p. 256-257° C.), digoxin, dihydroergotamine (m.p. 239° C.), dihydroergotoxin, diltiazem (m.p. 207-212° C.), dopamine antagonists, doxorubicin (m.p. 229-231° C.), econazole (m.p. 87° C.), endralazine (m.p. 185-188° C.), enkephalin, enalapril (m.p. 143-145° C.), epoprostenol, erythromycin, estradiol (m.p. 173-179° C.), estramustine (m.p. 104-105° C.), etofibrate (m.p. 100° C.), etoposide (m.p. 236-251° C.), factor ix, factor viii, felbamate (m.p. 151-152° C.), fenbendazole (m.p. 233° C.), fenofibrate (m.p. 79-82° C.), flunarizin (m.p. 252° C.), flurbiprofen (m.p. 110-111° C.), fluorometholone, 5-fluorouracil (m.p. 282-283° C.), flurazepam (m.p. 77-82° C.), fosfomycin (m.p. approx. 94° C.), fosmidomycin, furosemide (m.p. 206° C.), gallopamil, gamma interferon, ganciclovir, gentamicin (m.p. 102-108° C.), gepefrine (m.p. 155-158° C.), gliclazide (m.p. 180-182° C.), glipizide (m.p. 208-209° C.), griseofulvin (m.p. 220° C.), haptoglobulin, hepatitis B vaccine, hydralazine (m.p. 172-173° C.), hydrochlorothiazide (m.p. 273-275° C.), hydrocortisone (m.p. 212-220° C.), ibuprofen (m.p. 75-77° C.), ibuproxam (m.p. 119-121° C.), indinavir, indomethacin (m.p. 155° C.), iodinated aromatic x-ray contrast agents melting below 275° C. such as iodamide (m.p. 255-257° C.), ipratropium bromide (m.p. 230-232° C.), ketoconazole (m.p. 146° C.), ketoprofen (m.p. 94° C.), ketorolac, ketotifen (m.p. 152-153° C.), ketotifen fumarate (m.p. 192° C.), K-strophanthin (m.p. approx. 175° C.), labetalol, lactobacillus vaccine, Levocabastine HCl, levofloxacin, lidocaine (m.p. 68-69° C.), lidoflazin (m.p. 159-161° C.), lisuride (m.p. 186° C.), lisuride hydrogen maleate (m.p. 200° C.), lorazepam (m.p. 166-168° C.), loteprednol HCl, lovastatin, mefenamic acid (m.p. 230-231° C.), melphalan (m.p. 182-183° C.), memantin, mesulergin, metergoline (m.p. 146-149° C.), methotrexate (m.p. 185-204° C.), methyl digoxin (m.p. 227-231° C.), methylprednisolone (m.p. 228-237° C.), metronidazole (m.p. 158-160° C.), metisoprenol, metipranolol (m.p. 105-107° C.), metkephamide metolazone (m.p. 253-259° C.), metoprolol, metoprolol tartrate, miconazole (m.p. 135° C.), miconazole nitrate (m.p. 170 and 185° C.), minoxidil (m.p. 248° C.), misonidazol, molsidomin, nadolol (m.p. 124-136° C.), nafiverine (m.p. 220-221° C.), nafazatrom, naproxen (m.p. 155° C.), natural insulins, nepafenac, nesapidil, neomycin, nicardipine (m.p. 168-170° C.), nicorandil (m.p. 92-93° C.), nifedipine (m.p. 172-174° C.), niludipin, nimodipine, nitrazepam (m.p. 224-226° C.), nitrendipine, nitrocamptothesin, 9-nitrocamptothesin, oxazepam (m.p. 205-206° C.), oxprenolol (m.p. 78-80° C.), oxytetracycline (m.p. 181-182° C.), penicillins such as penicillin G benethamine (m.p. 147-147° C.), penecillin 0 (m.p. 79-81° C.), phenylbutazone (m.p. 105° C.), picotamide, pilocarpine, pindolol (m.p. 171-173° C.), piposulfan (m.p. 175-177° C.), piretanide (m.p. 225-227° C.), piribedil (m.p. 98° C.), piroxicam (m.p. 198-200° C.), pirprofen (m.p. 98-100° C.), plasminogenic activator, polymyxin b, prednisone, prednisolone (m.p. 240-241° C.), prednisone (m.p. 233-235° C.), pregnenolone (m.p. 193° C.), procarbacin, procaterol, progesterone (m.p. 121° C.), proinsulin, propafenone, propanolol, propentofyllin, propofol, propranolol (m.p. 96° C.), rifapentin, rimexolone, simvastatin, semi-synthetic insulins, sobrerol (m.p. 130° C.), somastotine and its derivatives, somatropin, stilamine, sulfinalol whose hydrochloride melts at 175° C., sulfinpyrazone (m.p. 136-137° C.), suloctidil (m.p. 62-63° C.), suprofen (m.p. 124° C.), sulproston, synthetic insulins, talinolol (m.p. 142-144° C.), taxol, taxotere, testosterone (m.p. 155° C.), testosterone propionate (m.p. 118-122° C.), testosterone undecanoate, tetracane HI (m.p. approx. 150° C.), tiaramide (HCl m.p. 159-161° C.), timolol, tolmetin (m.p. 155-157° C.), tranilast (m.p. 211-213° C.), travoprost, triquilar, tromantadine (HCl m.p. 157-158° C.), urokinase, valium (m.p. 125-126° C.), verapamil (m.p. 243-246° C.), vidarabine, vidarabine phosphate sodium salt, vinblastine (m.p. 211-216° C.), vinburin, vincamine (m.p. 232-233° C.), vincristine (m.p. 218-220° C.), vindesine (m.p. 230-232° C.), vinpocetine (m.p. 147-153° C.), vitamin A (m.p. 62-64° C.), vitamin E succinate (m.p. 76-78° C.), and x-ray contrast agents.

In certain embodiments, the poorly water soluble bioactive agent comprises an anti-neoplastic agent, an anti-inflammatory agent, or combinations thereof. In some embodiments, the poorly water soluble bioactive agent comprises a bioactive agent for the treatment, prevention, or diagnosis of a pulmonary disease or disorder, such as asthma or cystic fibrosis. For example, the poorly water soluble bioactive agent can comprise a bronchodilator, a vasodilator, a phosphodiesterase inhibitor, an endothelin receptor antagonist, an anti-inflammatory drugs, an anti-infective agent, a mucus-degrading agent, or combinations thereof. In some embodiments, the poorly water soluble bioactive agent comprises a bioactive agent for the treatment, prevention, or diagnosis of an ocular disease or disorder, such as age-related macular degeneration.

The amount of poorly water soluble bioactive agent present in the aqueous suspension can be varied. In some embodiments, the poorly water soluble bioactive agent is at least about 5% by weight of the aqueous suspension, based on the total weight of the aqueous suspension (e.g., at least about 10% by weight, at least about 15% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight, at least about 70% by weight, or at least about 75% by weight). In some embodiments, the poorly water soluble bioactive agent is about 80% or less by weight of the aqueous suspension, based on the total weight of the aqueous suspension (e.g., about 75% or less by weight, about 70% or less by weight, about 65% or less by weight, about 60% or less by weight, about 55% or less by weight, about 50% or less by weight, about 45% or less by weight, about 40% or less by weight, about 35% or less by weight, about 30% or less by weight, about 25% or less by weight, about 20% or less by weight, about 15% or less by weight, or about 10% or less by weight).

The amount of poorly water soluble bioactive agent present in the aqueous suspension can vary from any of the minimum described above to any of the maximum values described above. For example, the poorly water soluble bioactive agent can be present in an amount ranging from about 5% by weight to about 80% by weight of the aqueous suspension, based on the total weight of the aqueous suspension (e.g., from about 5% by weight to about 50% by weight, or from about 5% by weight to about 30% by weight).

The molten droplets of the poorly water soluble bioactive agent can be cooled using a variety of suitable methods. The cooling rate can be selected in order to influence the crystalline form of the poorly water soluble bioactive agent. For example, the molten droplets can be cooled slowly to select for crystalline micronized particles formed from a thermodynamically stable polymorph of the poorly water soluble bioactive agent. Alternatively, the molten droplets can be rapidly cooled to select for amorphous micronized particles formed from a poorly water soluble bioactive agent.

In some embodiments, the molten droplets are cooled instantly (i.e., flash frozen, for example, using a cryogenic liquid such as liquid nitrogen). In certain embodiments, the molten droplets are cooled by spraying the aqueous continuous phase. The aqueous continuous phase can be sprayed into a gas or liquid. In some embodiments, the molten droplets are cooled at a rate of at least about 0.1° C./minute (e.g., at least about 0.5° C./minute, at least about 1° C./minute, at least about 2° C./minute, at least about 3° C./minute, at least about 4° C./minute, at least about 5° C./minute, at least about 6° C./minute, at least about 7° C./minute, at least about 8° C./minute, at least about 9° C./minute, at least about 10° C./minute, at least about 15° C./minute, at least about 20° C./minute, at least about 25° C./minute, at least about 30° C./minute, at least about 35° C./minute, at least about 40° C./minute, at least about 45° C./minute, at least about 50° C./minute, at least about 75° C./minute, at least about 100° C./minute, at least about 125° C./minute, at least about 150° C./minute, or at least about 175° C./minute). In some embodiments, the molten droplets are cooled at a rate of about 200° C./minute or less (e.g., about 175° C./minute or less, about 150° C./minute or less, about 125° C./minute or less, about 100° C./minute or less, about 75° C./minute or less, about 50° C./minute or less, about 45° C./minute or less, about 40° C./minute or less, about 35° C./minute or less, about 30° C./minute or less, about 25° C./minute or less, about 20° C./minute or less, about 15° C./minute or less, about 10° C./minute or less, about 9° C./minute or less, about 8° C./minute or less, about 7° C./minute or less, about 6° C./minute or less, about 5° C./minute or less, about 4° C./minute or less, about 3° C./minute or less, about 2° C./minute or less, about 1° C./minute or less, or about 0.5° C./minute or less). The molten droplets are cooled at a rate ranging from any of the minimum rates described above to any of the maximum rates described above.

The molten droplets can be cooled at a linear or non-linear cooling rate. When the molten droplets are cooled at a linear cooling rate, the cooling rates described above can be cooling rates for a portion or an entirety of the cooling process. When the molten droplets are cooled at a non-linear cooling rate, the cooling rates described above can be average cooling rates for the cooling process.

In some embodiments, processes can further comprise reducing the size of the molten droplets while maintaining the superheated continuous phase at a temperature of from about 100° C. to about 280° C. and a pressure of from greater than standard pressure to about 1,000 psi. Suitable methods for reducing the size of the molten droplets can be selected in view of a number of factors, including the desired average particle size of the resulting micronized particles, the desired particle size distribution of the resulting Methods of reducing the size of the molten droplets can include stirring, shaking (including vibrational resonance mixing), agitating, vortexing (including crossflow vortex mixing), mixing, sonication (including acoustic resonance mixing), microfluidization, extrusion (e.g., membrane emulsification), spraying, injection, alteration of head pressure (e.g., rapidly decreasing head pressure over the continuous phase), or combinations thereof.

In some embodiments, reducing the size of the molten droplets comprises a low energy process. Low energy processes reduce the size of the molten droplets while imparting a low amount of mechanical energy to the continuous phase. In some embodiments, the amount of energy imparted to the continuous phase by the size reduction process is at least about 0.0005 J (e.g., at least about 0.001 J, at least about 0.005 J, at least about 0.01 J, at least about 0.05 J, at least about 0.1 J, at least about 0.5 J, at least about 1.0 J, at least about 1.5 J, at least about 2.0 J, at least about 2.5 J, at least about 3.0 J, at least about 3.5 J, at least about 4.0 J, or at least about 4.5 J). In some embodiments, the amount of energy imparted to the continuous phase by the size reduction process is about 5.0 J or less (e.g., about 4.5 J or less, about 4.0 J or less, about 3.5 J or less, about 3.0 J or less, about 2.5 J or less, about 2.0 J or less, about 1.5 J or less, about 1.0 J or less, about 0.5 J or less, about 0.1 J or less, about 0.05 J or less, about 0.01 J or less, about 0.005 J or less, or about 0.001 J or less).

The amount of energy imparted to the continuous phase by the size reduction process can range from any of the minimum values described above to any of the maximum values described above. For example, the amount of energy imparted to the continuous phase by the size reduction process can range from about 0.0005 J to about 5 J (e.g., from about 0.005 J to about 3 J).

In some embodiments, the method for reducing the size of the molten droplets includes mixing using a Hobart-type mixer or other mixer which includes rotating paddles, arms, or blades. The mixer using rotating paddles, arms, or blades can employ a speed of rotation for the paddles, arms, or blades in the range of about 500 to about 1,200 rpm for varying periods of time (e.g., mixing times ranging from 30 seconds to 30 minutes). In some embodiments, reducing the size of the molten droplets comprises low shear mixing. The mixing can involve a shear rate of at least about 10 reciprocal seconds (e.g., at least about 50 reciprocal seconds, at least about 100 reciprocal seconds, at least about 200 reciprocal seconds, at least about 250 reciprocal seconds, at least about 300 reciprocal seconds, at least about 400 reciprocal seconds, at least about 500 reciprocal seconds, at least about 600 reciprocal seconds, at least about 700 reciprocal seconds, at least about 750 reciprocal seconds, at least about 800 reciprocal seconds, or at least about 900 reciprocal seconds). The mixing can involve a shear rate of about 1000 reciprocal seconds or less (e.g., about 900 reciprocal seconds or less, about 800 reciprocal seconds or less, about 750 reciprocal seconds or less, about 700 reciprocal seconds or less, about 600 reciprocal seconds or less, about 500 reciprocal seconds or less, about 400 reciprocal seconds or less, about 300 reciprocal seconds or less, about 250 reciprocal seconds or less, about 200 reciprocal seconds or less, about 100 reciprocal seconds or less, or about 50 reciprocal seconds or less).

The mixing can involve a shear rate ranging from any of the minimum values described above to any of the maximum values described above. For example, the mixing can involve a shear rate ranging from about 10 reciprocal seconds to about 1000 reciprocal seconds (e.g., from about 50 reciprocal seconds to about 500 reciprocal seconds, or from about 50 reciprocal seconds to about 250 reciprocal seconds).

In certain embodiments, a second poorly water soluble bioactive agent is added to the aqueous suspension, to the superheated continuous phase, or combinations thereof. The second poorly water soluble bioactive agent can have a higher melting point than the first poorly water soluble bioactive agent. The aqueous suspension can be heated to a temperature greater than the melting point of both the first and the second poorly water soluble bioactive agent. Alternatively, the aqueous suspension can be heated to a temperature ranging from the melting point of the first poorly water soluble bioactive agent to less than the melting point of the second poorly water soluble bioactive agent. In these embodiments, molten droplets of the first poorly water soluble bioactive agent serve as a solvent in which the second poorly water soluble bioactive agent is dissolved or dispersed. In certain cases, the second poorly water soluble bioactive agent dissolves in the molten droplets of the first poorly water soluble bioactive agent, and step (b) comprises cooling the molten droplets to form micronized particles comprising the first poorly water soluble bioactive agent and the second poorly water soluble bioactive agent. In other cases, the second poorly water soluble bioactive agent becomes dispersed in the molten droplets of the first poorly water soluble bioactive agent, and step (b) comprises cooling the molten droplets to form micronized particles comprising the first poorly water soluble bioactive agent and the second poorly water soluble bioactive agent.

By way of example, a first poorly water soluble bioactive agent (e.g., ibuprofen; melting point of 75° C.) may be suspended in water and heated to a temperature of from about 100° C. to about 240° C. at a pressure of from greater than standard pressure to about 1,000 psi to form a superheated continuous phase comprising molten droplets of ibuprofen. Ciprofloxacin can be added to the aqueous suspension of ibuprofen or to the superheated continuous phase. Ciprofloxacin melts with decomposition at approximately 250° C., and thus is not amenable to melt processing; however, ciprofloxacin dissolves in the molten droplets of ibuprofen. The molten droplets can then be cooled to form micronized particles comprising a homogeneous mixture of ibuprofen and ciprofloxacin. This methodology can be used to prepare micronized particles for the co-delivery of multiple bioactive agents with a co-controlled release profile.

The aqueous suspension can comprise water, Ringer's solution, phosphate buffered saline (PBS), or isotonic sodium chloride solution. If desired, the aqueous suspension can further comprises an excipient. Representative excipients include solvents, diluents, pH modifying agents, preservatives, antioxidants, suspending agents, wetting agents, viscosity modifiers, tonicity agents, stabilizers, and combinations thereof. Suitable pharmaceutically acceptable excipients are preferably selected from materials which are generally recognized as safe (GRAS), and may be administered to an individual without causing undesirable biological side effects or unwanted interactions.

In variations of the processes described above, the poorly water soluble bioactive agent can be melted prior to addition to the aqueous phase. Thus, also provided are processes for preparing micronized particles comprising a poorly water soluble bioactive agent which comprise (a) melting the poorly water soluble bioactive agent, (b) introducing the melted poorly water soluble bioactive agent into a superheated aqueous phase heated to a temperature of from about 100° C. to about 280° C. at a pressure of from greater than standard pressure to about 1,000 PSI to form a superheated continuous phase comprising molten droplets of the poorly water soluble bioactive agent dispersed in superheated water, and (c) cooling the molten droplets to form micronized particles comprising the poorly water soluble bioactive agent. In certain embodiments, step (b) comprises a superheated aqueous phase heated to a temperature ranging from the melting point of the poorly water soluble bioactive agent to 20° C. higher than the melting point of the poorly water soluble bioactive agent (e.g., heated to a temperature ranging from the melting point of the poorly water soluble bioactive agent to 10° C. higher than the melting point of the poorly water soluble bioactive agent).

Introducing the melted poorly water soluble bioactive agent into the superheated aqueous phase can comprise injecting droplets of the melted poorly water soluble bioactive agent into the superheated aqueous phase. Injecting droplets of the melted poorly water soluble bioactive agent into the superheated aqueous phase can comprise spraying the melted poorly water soluble bioactive agent into the superheated aqueous phase. Injecting droplets of the melted poorly water soluble bioactive agent into the superheated aqueous phase can comprise extruding the melted poorly water soluble bioactive agent into the superheated aqueous phase. For example, the melted poorly water soluble bioactive agent can be extruded into the superheated aqueous phase through a microporous membrane (i.e., membrane emulsification). In certain embodiments, the superheated aqueous phase is flowing orthogonally to the surface of the microporous membrane during extrusion of the melted poorly water soluble bioactive agent into the superheated aqueous phase (i.e., cross-flow membrane emulsification).

In variations of the processes described above, a matrix material and a poorly water soluble bioactive agent are added to the aqueous phase. These processes can be used to form micronized particles comprising a mixture of a matrix material and a poorly water soluble bioactive agent. Thus, also provided are processes for preparing micronized particles comprising a poorly water soluble bioactive agent that can comprise (a) heating an aqueous suspension comprising a matrix material and the poorly water soluble bioactive agent to a temperature of from about 100° C. to about 280° C. at a pressure of from greater than standard pressure to about 1,000 PSI to form a superheated continuous phase comprising molten droplets of the matrix material dispersed in superheated water, and (b) cooling the molten droplets to form micronized particles comprising the matrix material and the poorly water soluble bioactive agent. In certain embodiments, step (a) comprises heating the aqueous suspension to a temperature ranging from the melting point of the matrix material to 10° C. higher than the melting point of the matrix material.

Any suitable matrix material can be used. The matrix material can be, for example, a polymer, wax, or lipid which provides for the controlled release of the poorly water soluble bioactive agent. Examples of suitable matrix materials include cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein; shellac; alginic acid; poly(lactic acid) (PLA), poly(lactic-co-glycolic acid) (PLGA), poly(lactic acid)-polyethyleneglycol (PLA-PEG) block copolymers, polyanhydrides, poly(ester anhydrides), ppolyglycolide (PGA), poly-3-hydroxybutyrate (PHB) and copolymers thereof, poly-4-hydroxybutyrate (P4HB), polycaprolactone, waxes, such as spermaceti, beeswax, and carnuba wax, long chain lipid mixtures, such as gelucires (i.e., polyethylene glycol glycerides composed of mono-, di- and triglycerides and mono- and diesters of PEG), lauroyl macrogol-32 glycerides, lauroyl polyoxyl-32 glycerides, and lauroyl polyoxylglycerides, long chain alcohols, such as cetyl alcohol, long chain fatty acids, such as behinic acid, and combinations thereof.

The poorly water soluble bioactive agent can have a higher melting point than the matrix material. The aqueous suspension can be heated to a temperature greater than the melting point of both the matrix material and the poorly water soluble bioactive agent. Alternatively, the aqueous suspension can be heated to a temperature ranging from the melting point of the matrix material to less than the melting point of the poorly water soluble bioactive agent. In these embodiments, molten droplets of the matrix material can serve as a solvent in which the poorly water soluble bioactive agent is dissolved or dispersed. In certain cases, the poorly water soluble bioactive agent dissolves in the molten droplets of the matrix material, and step (b) comprises cooling the molten droplets to form micronized particles comprising the first poorly water soluble bioactive agent and the second poorly water soluble bioactive agent. In other cases, the poorly water soluble bioactive agent becomes dispersed in the molten droplets of the matrix material, and step (b) comprises cooling the molten droplets to form micronized particles comprising the first poorly water soluble bioactive agent and the second poorly water soluble bioactive agent.

Once formed by any of the processes described above, the micronized particles can be dried using methods known in the art. Drying the micronized particles can involve separating the micronized particles from the aqueous phase in which they are dispersed. Drying the micronized particles can involve further drying the separated micronized particles to reduce residual water content of the micronized particles. In certain cases, the micronized particles are dried, meaning that the micronized particles have a water content ranging from 0% by weight to about 5% by weight, based on the total weight of the micronized particles. For example, dried micronized particles can have a water content of about 5% or less by weight, based on the total weight of the micronized particles (e.g., about 4% or less by weight, about 3% or less by weight, about 2% or less by weight, about 1% or less by weight, or about 0.5% or less). In some embodiments, the micronized particles have a water content ranging from about 0.1% by weight to about 3% by weight, based on the total weight of the micronized particles (e.g., from about 0.1% by weight to about 2% by weight, or from about 0.1% by weight to about 1% by weight). Suitable methods for drying the micronized particles include spray drying (including steam drying), lyophilizing, filtration, or combinations thereof. In certain embodiments, the micronized particles are dried by spray drying.

Once formed, the micronized particles can be stabilized. Stabilizing the micronized particles can comprise contacting the micronized particles with a stabilizer, such as a surfactant, polymer, or combination thereof. Examples of suitable stabilizers include include natural surfactants, such as casein, gelatin, tragacanth, waxes, enteric resins, paraffin, acacia, gelatin, cholesterol esters and triglycerides; nonionic surfactants such as polyoxyethylene fatty alcohol ethers, sorbitan fatty acid esters, polyoxyethylene fatty acid esters, sorbitan esters, glycerol monostearate, polyethylene glycols, cetyl alcohol, cetostearyl alcohol, stearyl alcohol, poloxamers, polaxamines, methylcellulose, ethylcellulose, hydroxycellulose, hydroxy propylcellulose, hydroxy propylmethylcellulose, noncrystalline cellulose, polyvinyl alcohol, polyvinylpyrrolidone, and synthetic phospholipids; anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their salts), and negatively charged glyceryl esters, sodium carboxymethylcellulose, and calcium carboxymethylcellulose; cationic surfactants such as quaternary ammonium compounds, benzalkonium chloride, cetyltrimethylammonium bromide, chitosans and lauryldimethylbenzylammonium chloride; colloidal clays such as bentonite and veegum; and combinations thereof.

If desired, the micronized particles can be coated with a controlled release material to modulate dissolution of the micronized particles. Suitable controlled release materials are known in the art, and include cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein; shellac; alginic acid; poly(lactic acid) (PLA), poly(lactic-co-glycolic acid) (PLGA), poly(lactic acid)-polyethyleneglycol (PLA-PEG) block copolymers, polyanhydrides, poly(ester anhydrides), ppolyglycolide (PGA), poly-3-hydroxybutyrate (PHB) and copolymers thereof, poly-4-hydroxybutyrate (P4HB), polycaprolactone, waxes, such as spermaceti, beeswax, and carnuba wax, long chain lipid mixtures, such as gelucires (i.e., polyethylene glycol glycerides composed of mono-, di- and triglycerides and mono- and diesters of PEG), lauroyl macrogol-32 glycerides, lauroyl polyoxyl-32 glycerides, and lauroyl polyoxylglycerides, long chain alcohols, such as cetyl alcohol, long chain fatty acids, such as behinic acid, and combinations thereof.

The resulting micronized particles can be amorphous or crystalline. In some embodiments, the micronized particles are substantially free of organic solvents. In some embodiments, the micronized particles are monodisperse in size. A population of particles can be said to be monodisperse when the particles in the population have the same or nearly the same particle size. The term monodisperse can refer to particle distributions in which 90% of the distribution lies within 5% of the average particle size. The average particle size refers to the statistical mean particle size (diameter) of the particles in a population of particles. The diameter of an essentially spherical particle can refer to the physical or hydrodynamic diameter. The diameter of a non-spherical particle can refer to the largest linear distance between two points on the surface of the particle. The average particle size can be measured using methods known in the art, such as dynamic light scattering.

In some embodiments, the micronized particles prepared using the processes described herein have an average particle size of at least about 50 nm (e.g., at least about 200 nm, at least about 300 nm, at least about 400 nm, at least about 500 nm, at least about 600 nm, at least about 700 nm, at least about 800 nm, at least about 900 nm, at least about 1 micron, at least about 2 microns, at least about 3 microns, at least about 4 microns, at least about 5 microns, at least about 6 microns, at least about 7 microns, at least about 8 microns, at least about 9 microns, at least about 10 microns, at least about 15 microns, at least about 20 microns, at least about 25 microns, at least about 30 microns, at least about 35 microns, at least about 40 microns, at least about 45 microns, at least about 50 microns, or at least about 55 microns). In some embodiments, the micronized particles prepared using the processes described herein have an average particle size of about 60 microns or less (e.g., about 55 microns or less, about 50 microns or less, about 45 microns or less, about 40 microns or less, about 35 microns or less, about 30 microns or less, about 25 microns or less, about 20 microns or less, about 15 microns or less, about 10 microns or less, about 9 microns or less, about 8 microns or less, about 7 microns or less, about 6 microns or less, about 5 microns or less, about 4 microns or less, about 3 microns or less, about 2 microns or less, about 1 micron or less, about 900 nm or less, about 800 nm or less, about 700 nm or less, about 600 nm or less, about 500 nm or less, about 400 nm or less, about 300 nm or less, about 200 nm or less, or about 100 nm or less).

The micronized particles prepared using the processes described herein can have an average particle size ranging from any of the minimum values described above to any of the maximum values described above. For example, the micronized particles prepared using the processes described herein can have an average particle size ranging from about 50 nm to about 60 microns (e.g., from about 50 nm to about 1 micron, from about 1 micron to about 5 microns, or from about 1 micron to about 20 microns The particle size and particle size distribution of the resulting micronized particles can be selected in view of the desired therapeutic application. For example, in certain embodiments, the micronized particles comprise a poorly water soluble bioactive agent for the treatment, prevention, or diagnosis of a pulmonary disease or disorder, such as asthma or cystic fibrosis. In these embodiments, the particle size and particle size distribution of the micronized particles can be selected to facilitate pulmonary delivery.

The respiratory tract is the structure involved in the exchange of gases between the atmosphere and the blood stream. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung, where the exchange of gases occurs.

The alveolar surface area is the largest in the respiratory system and is where drug absorption occurs. The alveoli are covered by a thin epithelium without cilia or a mucus blanket and secrete surfactant phospholipids. Effective delivery of therapeutic agents via pulmonary routes requires that the active agent be formulated so as to reach the alveoli.

Particle morphology affects the depth of penetration of a particle into the lung, as well as uptake of the bioactive agent particle once delivered to the lung. For the treatment, prevention, or diagnosis of many pulmonary diseases or disorders, drug particles should reach the alveoli to maximize therapeutic efficacy. Accordingly, the micronized particles can be selected to have the appropriate mass median aerodynamic diameter (MMAD), tap density, and surface roughness to achieve delivery of the one or more active agents to the deep lung. Preferred particle morphologies for delivery to the deep lung are known in the art, and are described, for example, in U.S. Pat. No. 7,052,678 to Vanbever, et al.

"Mass Median Aerodynamic Diameter" (MMAD), as used herein, refers to the median aerodynamic size of a plurality of particles. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle.

MMAD can be experimentally determined by methods known in the art, such as by cascade impaction.

"Tap Density", as used herein, refers to a measure of the density of a powder, such as a population of micronized particles. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure.

Particles having a mass median aerodynamic diameter (MMAD) of greater than about 5 microns generally do not reach the lung; instead, they tend to impact the back of the throat and are swallowed. Particles having diameters of about 3 to about 5 microns are small enough to reach the upper- to mid-pulmonary region (conducting airways), but may be too large to reach the alveoli. Smaller particles, (i.e., about 0.5 to about 3 microns), are capable of efficiently reaching the alveolar region. Particles having diameters smaller than about 0.5 microns can also be deposited in the alveolar region by sedimentation, although very small particles may be exhaled.

The precise particle size range effective to achieve delivery to the alveolar region will depend on several factors, including the tap density of particles being delivered. Generally speaking, as tap density decreases, the MMAD of particles capable of efficiently reaching the alveolar region of the lungs increases. Therefore, in cases of particles with low tap densities, particles having diameters of about 3 to about 5 microns, about 5 to about 7 microns, or about 7 to about 9.5 microns can be efficiently delivered to the lungs. A suitable aerodynamic diameter for maximum deposition within the lungs can be calculated. See, for example, U.S. Pat. No. 7,052,678 to Vanbever, et al.

In some embodiments, the micronized particles comprise a population of particles having a median mass aerodynamic diameter from about 0.5 to about 10 microns (e.g., from about 0.5 microns to about 7 microns, or from about 0.5 to about 5 microns). In some embodiments, the micronized particles comprise a population of particles having a median mass aerodynamic diameter from about 0.5 to about 3 microns. In some embodiments, the micronized particles comprise a population of particles having a median mass aerodynamic diameter from about 3 to about 5 microns. In some embodiments, the micronized particles comprise a population of particles having a median mass aerodynamic diameter from about 5 to about 7 microns. In some embodiments, the micronized particles comprise a population of particles having a median mass aerodynamic diameter from about 7 to about 9.5 microns.

In some cases, there may be an advantage to delivering particles larger than about 3 microns in diameter. Phagocytosis of particles by alveolar macrophages diminishes precipitously as particle diameter increases beyond about 3 microns. Kawaguchi, H., et al., Biomaterials 7: 61-66 (1986); Krenis, L. J. and Strauss, B., Proc. Soc. Exp. Med., 107: 748-750 (1961); and Rudt, S, and Muller, R. H., J. Contr. Rel, 22: 263-272 (1992). By administering particles with an aerodynamic volume greater than 3 microns, phagocytic engulfment by alveolar macrophages and clearance from the lungs can be minimized.

In some embodiments, at least about 80% (e.g., at least about 85%, at least about 90%, or at least about 95%) of the micronized particles in the population of particles have aerodynamic diameter of less than about 10 microns (e.g., less than about 7 microns, or less than about 5 microns). In some embodiments, at least about 80% (e.g., at least about 85%, at least about 90%, or at least about 95%) of the micronized particles in the population of particles have aerodynamic diameter greater than about 0.5 microns. In some embodiments, at least about 80% (e.g., at least about 85%, at least about 90%, or at least about 95%) of the micronized particles in the population of particles have aerodynamic diameter greater than about 0.1 microns.

In some embodiments, at least about 80% (e.g., at least about 85%, at least about 90%, or at least about 95%) of the micronized particles in the population of particles have aerodynamic diameter ranging from about 0.5 microns to about 10 microns (e.g., from about 0.5 microns to about 7 microns, from about 0.5 microns to about 5 microns). In some embodiments, at least about 80% (e.g., at least about 85%, at least about 90%, or at least about 95%) of the micronized particles in the population of particles have aerodynamic diameter ranging from about 0.5 microns to about 3 microns. In some embodiments, at least about 80% (e.g., at least about 85%, at least about 90%, or at least about 95%) of the micronized particles in the population of particles have aerodynamic diameter ranging from about 3 microns to about 5 microns. In some embodiments, at least about 80% (e.g., at least about 85%, at least about 90%, or at least about 95%) of the micronized particles in the population of particles have aerodynamic diameter ranging from about 5 microns to about 7 microns. In some embodiments, at least about 80% (e.g., at least about 85%, at least about 90%, or at least about 95%) of the micronized particles in the population of particles have aerodynamic diameter ranging from about 7 microns to about 9.5 microns.

In some embodiments, the micronized particles can have a tap density of less than about 0.4 g/cm$^3$ (e.g., less than about 0.25 g/cm$^3$, or less than about 0.1 g/cm$^3$). Features which can contribute to low tap density include irregular surface texture and porous structure. In some cases, the micronized particles are spherical or ovoid in shape. The micronized particles can have a smooth or rough surface texture.

Also provided are pharmaceutical formulations including micronized particles prepared using the processes described herein. Pharmaceutical formulations can include micronized particles in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials that are generally recognized as safe (GRAS), and may be administered to an individual without causing undesirable biological side effects or unwanted interactions. The micronized particles can be formulated for a variety of routes of administration and/or applications. Suitable routes of administration include enteral, parenteral, pulmonary, and topical.

Suitable oral dosage forms include tablets, capsules, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art. Oral dosage forms, such as capsules, tablets, and suspensions, can for formulated for controlled release (e.g., immediate release, delayed release, extended release, pulsatile release, and combinations thereof) using methods known in the art.

The micronized particles can also be formulated for parenteral administration. Parenteral administration refers to administration by any method other than through the digestive tract or non-invasive topical or regional routes. For example, parenteral administration can include administration to a patient intravenously, intradermally, intraperitoneally, intrapleurally, intratracheally, intramuscularly, subcutaneously, by injection, and by infusion. Parenteral formulations can be prepared as aqueous compositions using techniques is known in the art. Typically, such compositions can be prepared as injectable formulations, such as, for example, particle suspensions; solid forms suitable for using to prepare suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride. The parenteral formulations described herein can be formulated for controlled release including immediate release, delayed release, extended release, pulsatile release, and combinations thereof.

In certain embodiments, the micronized particles can be formulated as suspension for injection to the eye. Pharmaceutical formulations for ocular administration are preferably in the form of a sterile aqueous solution or suspension of particles formed from one or more polymer-drug conjugates. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

In certain embodiments, the micronized particles can be formulated for pulmonary administration. When formulated for pulmonary administration, the micronized particles can have the particle size and particle size distribution described above. The micronized particles can be administered to the lungs as dry powder using suitable methods known in the art (e.g., a dry powder inhaler). Alternatively, the micronized particles can be suspended in a liquid formulation, and administered to the lung using methods known in the art for the delivery of liquid formulations to the lungs (e.g., pressurized metered dose inhaler, nebulizer, or electrohydrodynamic aerosol device).

The processes described herein can also be utilized to prepare micronized particles of bioactive agents for non-pharmaceutical uses. For example, the methods described herein can be utilized to prepare micronized particles of poorly water soluble agrichemicals, such as pesticides, which can be administered in agricultural settings.

EXAMPLES

Example 1

Preparation of Ibuprofen Particles

Tween® polysorbate 80 was dissolved/dispersed at a 0.05-0/5% W/V concentration in distilled water. The mixture was then pre-heated to around melting point of Ibuprofen (~77° C.). Ibuprofen was then dispersed into the aqueous phase in an amount effective to achieve an ibuprofen concentration of between 0.05 and 1% W/V. The mixture was then stirred under high heat until a pre-emulsion was formed.

A pressure vessel lid was added to seal the reaction vessel, and the mixture was heated. Upon heating, the pressure inside the reaction vessel increased. The resultant increase in pressure in the reaction vessel increased the boiling point of the aqueous phase. The mixture was stirred until mixture reached a temperature at which the viscosity of the dispersed oil phase (ibuprofen) was low enough to permit the molten ibuprofen droplets to be reduced in size with simple stirring (a pressure of approximately 25 psi and a corresponding temperature of approximately 116° C.).

The molten droplets were subsequently cooled to form micronized ibuprofen particles. Micronized particles could be formed draining the molten emulsion through a cooling tube and/or flash cooled/diluted into a surfactant-containing aqueous liquid. Micronized particles could also be formed by cooling the molten emulsion to room temperature under stirring or under ice.

Figure 1:
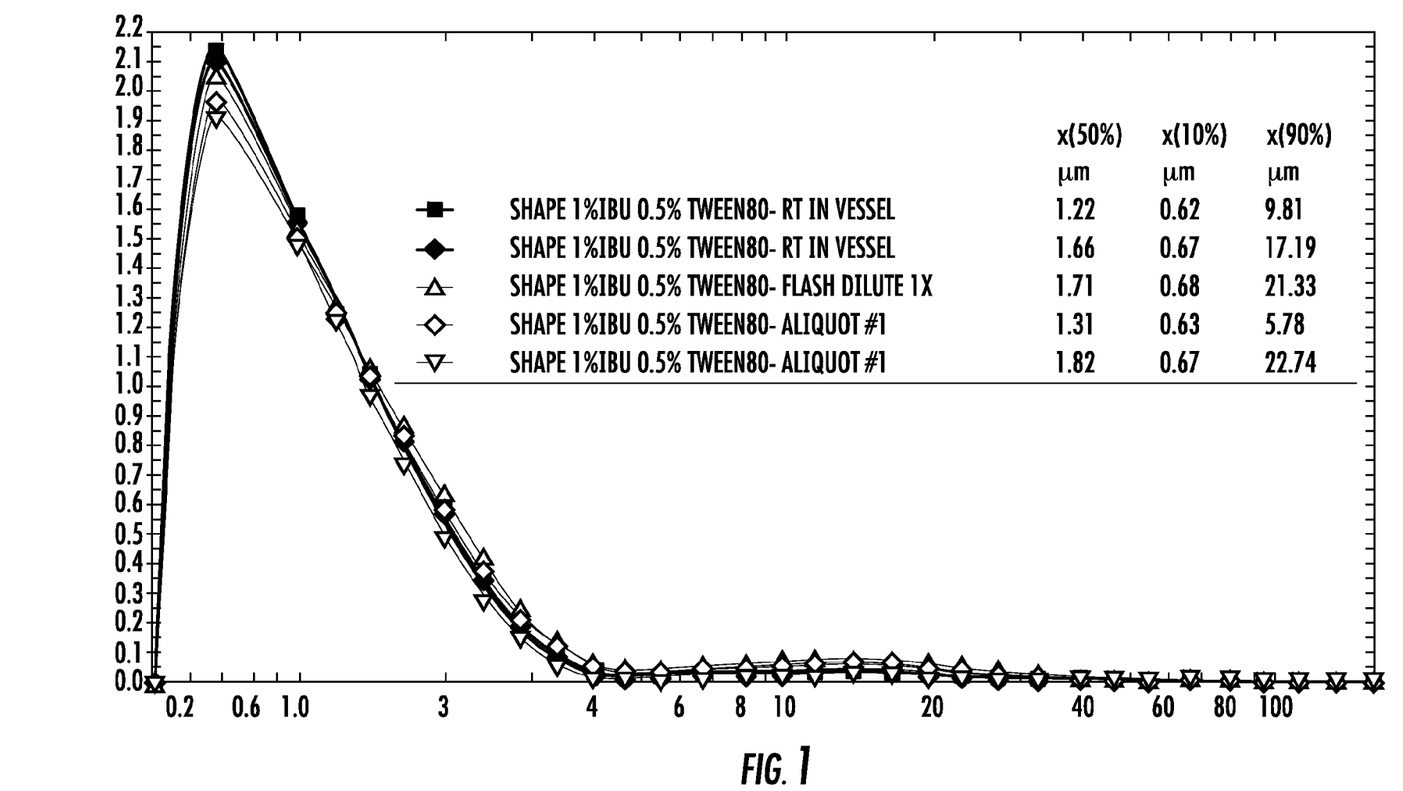
FIG. 1 is plot of the particle size distribution of populations of micronized particles prepared from ibuprofen.

Each of these methods yielded micronized ibuprofen particles with different characteristics. Flash/cooling and dilution resulted in partial dissolution of the ibuprofen, and formed micronized particles in the form of very fine needles. Cooling the molten emulsion to room temperature under stirring or under ice afforded stable micro and nano-suspensions of micronized ibuprofen particles. Samples were analyzed using a Sympatac® laser diffraction apparatus. The results of this analysis are shown in FIG. 1.

Example 2

Preparation of Ibuprofen+Ciprofloxacin Particles 300 mg of ibuprofen was heated in a beaker under stirring to melt. Once molten, lecithin was added to the molten ibuprofen to form a 0.01-5% W/V emulsion of lecithin in ibuprofen. 200 mg ciprofloxacin was then added to the molten dispersion of ibuprofen and lecithin. Once a clear molten solution was formed, approximately 50 mL deionized water (preheated to 80° C.) was added to the mixture. The mixture was stirred at an elevated temperature until a homogenous emulsion was formed. The emulsion was subsequently cooled to room temperature, and lyophilized or centrifuged to retrieve micronized particles.

Figure 2:
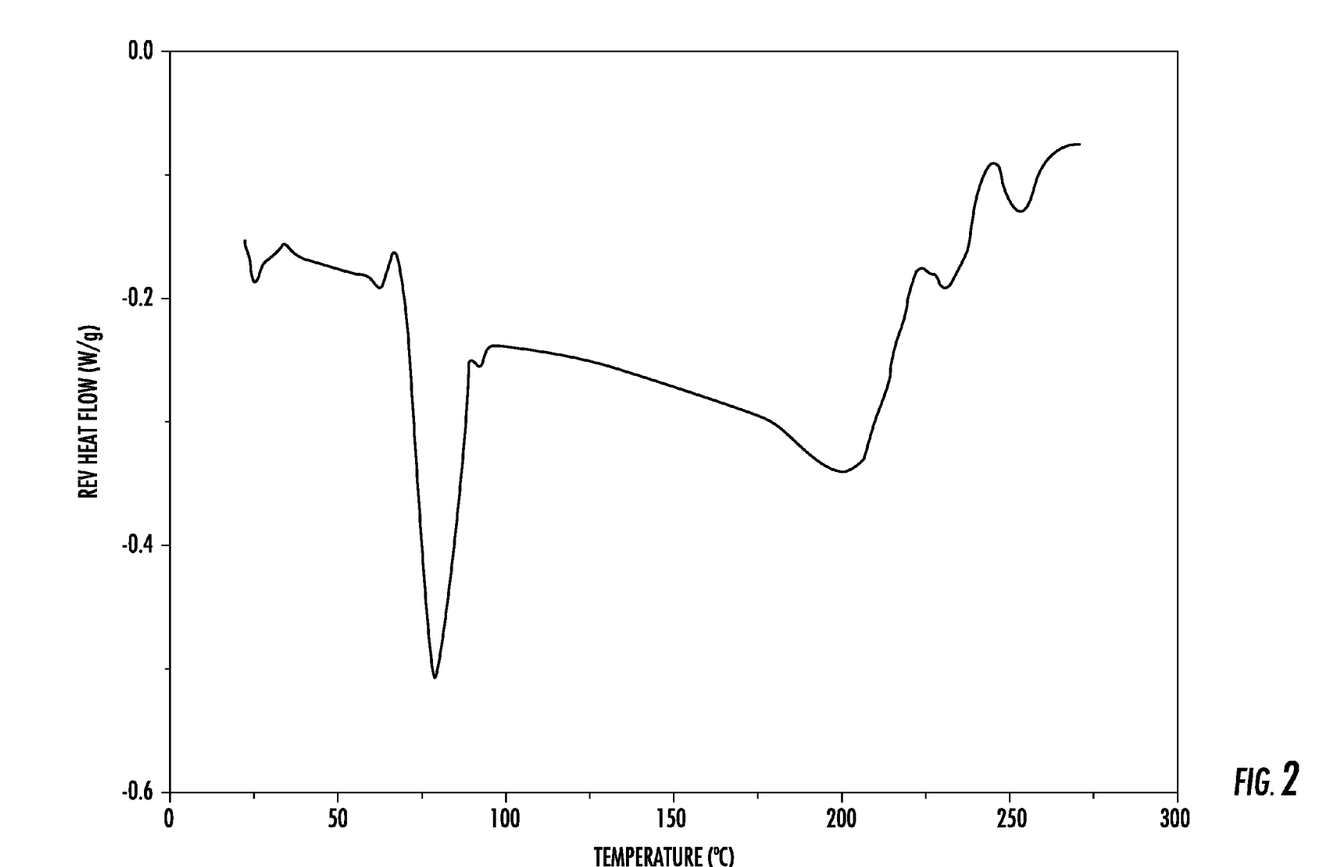
FIG. 2 is a differential scanning calorimetry (DSC) curve of a 2:3 physical mixture of ciprofloxacin/ibuprofen.
Figure 3:
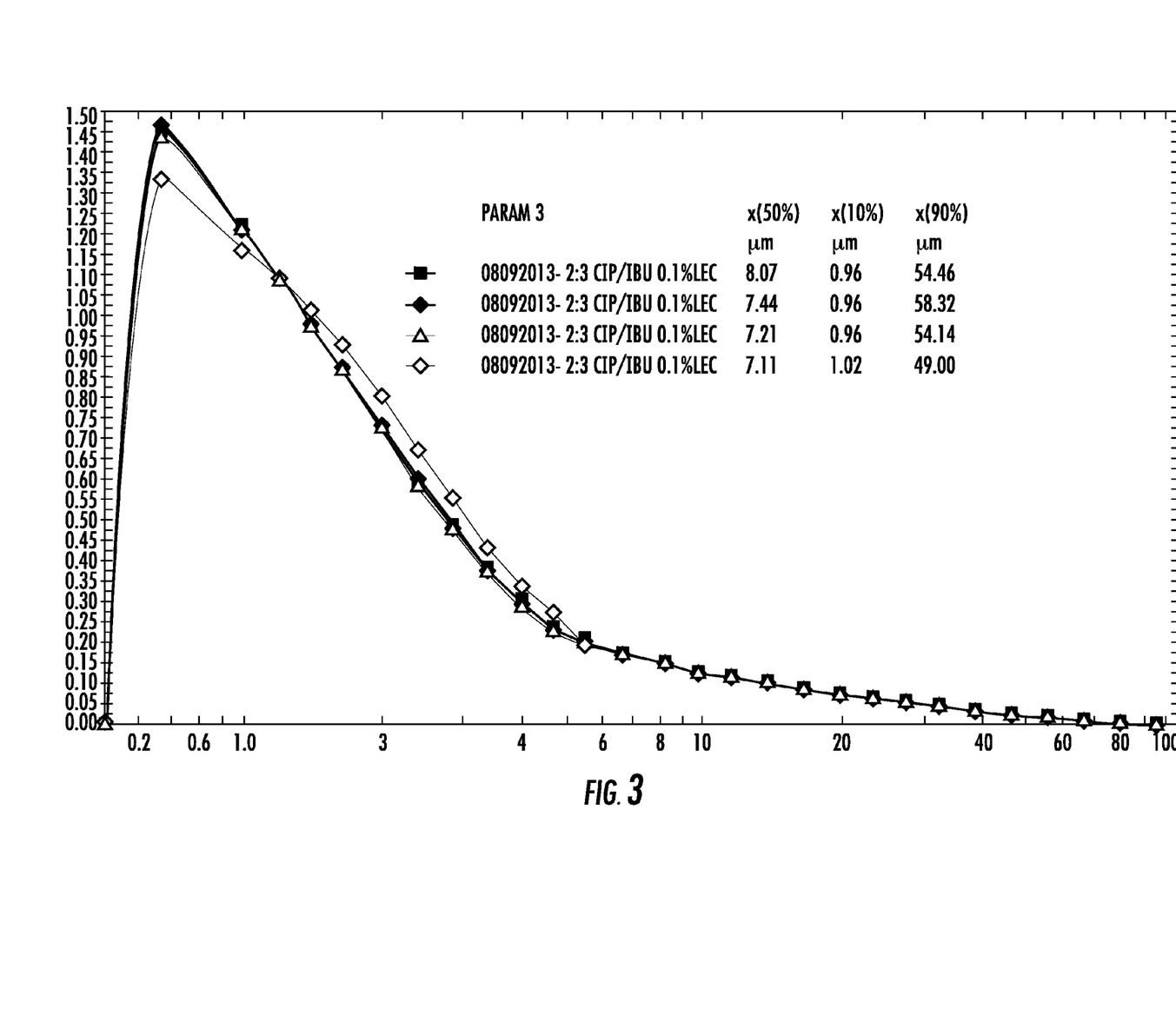
FIG. 3 is plot of the particle size distribution of populations of micronized particles prepared from a 2:3 physical mixture of ciprofloxacin/ibuprofen.

Differential scanning calorimetry (DSC) was used to confirm the molten miscibility of ciprofloxacin and ibuprofen, as indicated by a depression and widening of the ciprofloxacin melting endotherm (from 255° C. to ~210° C.) in the presence of ibuprofen (melting endotherm at 77° C.) in a 2:3 physical mixture of ciprofloxacin/ibuprofen. See FIG. 2. Particle size analysis (laser diffraction analysis using a Sympatac® laser diffraction apparatus) was conducted on a resuspended lyophylate of a 2:3 mixture of ciprofloxacin/ibuprofen. The results of this analysis are shown in FIG. 3. Particle size analysis revealed that a majority of the particles had a particle size below 1 micron. These results demonstrate the feasibility of utilizing a first drug having a lower melting point drug as a dissolution carrier or solvent for second drug having has a higher melting point.

The processes and compositions of the appended claims are not limited in scope by the specific processes and compositions described herein, which are intended as illustrations of a few aspects of the claims. Any processes and compositions that are functionally equivalent are intended to fall within the scope of the claims. Various modifications of the processes and compositions in addition to those shown and described herein are intended to fall within the scope of the appended claims. Further, while only certain representative processes and compositions disclosed herein are specifically described, other combinations of the processes and compositions also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A process for preparing micronized particles comprising a poorly water soluble bioactive agent, the process comprising
    (a) heating an aqueous suspension comprising the poorly water soluble bioactive agent to a temperature of from about 100° C. to about 280° C. at a pressure of from greater than standard pressure to about 1,000 psi to form a superheated continuous phase comprising molten droplets of the poorly water soluble bioactive agent dispersed in superheated water;
    (b) reducing the size of the molten droplets while maintaining the superheated continuous phase at a temperature of from about 100° C. to about 280° C. and a pressure of from greater than standard pressure to about 1,000 psi, wherein reducing the size of the molten droplets comprises a low energy process; and
    (c) cooling the molten droplets to form micronized particles comprising the poorly water soluble bioactive agent.

2. The process of claim 1, wherein reducing the size of the molten droplets comprises low shear mixing.

3. The process of claim 1, further comprising drying the micronized particles.

4. The process of claim 1, further comprising stabilizing the micronized particles.

5. The process of claim 1, wherein cooling the molten droplets comprises cooling the molten droplets at a rate effective to form micronized particles comprising a crystalline form of the poorly water soluble bioactive agent.

6. The process of claim 1, wherein the micronized particles have an average particle size ranging from about 1 micron to about 5 microns.

7. The process of claim 1, wherein the poorly water soluble bioactive agent has a solubility in water of about 5 mg/mL or less at 25° C.

8. The process of claim 1, wherein the poorly water soluble bioactive agent has a melting point of from about 100° C. to about 280° C., and
    wherein step (a) comprises heating the aqueous suspension to a temperature ranging from the melting point of the poorly water soluble bioactive agent to about 10° C. higher than the melting point of the poorly water soluble bioactive agent.

9. The process of claim 1, further comprising adding a second poorly water soluble bioactive agent to the aqueous suspension, to the superheated continuous phase, or combinations thereof.

10. The process of claim 9, wherein step (b) comprises a superheated aqueous phase heated to a temperature ranging from the melting point of the first poorly water soluble bioactive agent to less than the melting point of the second poorly water soluble bioactive agent.

11. A process for preparing micronized particles comprising a poorly water soluble bioactive agent, the process comprising
    (a) melting the poorly water soluble bioactive agent;
    (b) introducing the melted poorly water soluble bioactive agent into a superheated aqueous phase heated to a temperature of from about 100° C. to about 280° C. at a pressure of from greater than standard pressure to about 1,000 psi to form a superheated continuous phase comprising molten droplets of the poorly water soluble bioactive agent dispersed in superheated water, and
    (c) cooling the molten droplets to form micronized particles comprising the poorly water soluble bioactive agent.

12. The process of claim 11, wherein introducing the melted poorly water soluble bioactive agent into the superheated aqueous phase comprises injecting droplets of the melted poorly water soluble bioactive agent into the superheated aqueous phase.

13. The process of claim 12, wherein injecting droplets of the melted poorly water soluble bioactive agent into the superheated aqueous phase comprises spraying the melted poorly water soluble bioactive agent into the superheated aqueous phase.

14. The process of claim 12, wherein injecting droplets of the melted poorly water soluble bioactive agent into the superheated aqueous phase comprises extruding the melted poorly water soluble bioactive agent into the superheated aqueous phase through a microporous membrane.

15. The process of claim 14, wherein injecting droplets of the melted poorly water soluble bioactive agent into the superheated aqueous phase comprises cross-flow membrane emulsification.

16. A process for preparing micronized particles comprising a poorly water soluble bioactive agent, the process comprising
    (a) heating an aqueous suspension comprising a matrix material and the poorly water soluble bioactive agent to a temperature of from about 100° C. to about 280° C. at a pressure of from greater than standard pressure to about 1,000 psi to form a superheated continuous phase comprising molten droplets of the matrix material dispersed in superheated water, and
    (b) cooling the molten droplets to form micronized particles comprising the matrix material and the poorly water soluble bioactive agent.

17. The process of claim 16, wherein the poorly water soluble bioactive agent has a higher melting point than the matrix material, and wherein step (a) comprises heating the aqueous suspension to a temperature ranging from the melting point of the matrix material to less than the melting point of the poorly water soluble bioactive agent.

18. The process of claim 16, wherein the matrix material has a melting point of from about 100° C. to about 280° C., and wherein step (a) comprises heating the aqueous suspension to a temperature ranging from the melting point of the matrix material to about 10° C. higher than the melting point of the matrix material.

19. A process for preparing micronized particles comprising a poorly water soluble bioactive agent, the process comprising
    (a) heating an aqueous suspension comprising the poorly water soluble bioactive agent to a temperature of from about 100° C. to about 280° C. at a pressure of from greater than standard pressure to about 1,000 psi to form a superheated continuous phase comprising molten droplets of the poorly water soluble bioactive agent dispersed in superheated water;
    (b) adding a second poorly water soluble bioactive agent to the aqueous suspension, to the superheated continuous phase, or combinations thereof; and
    (c) cooling the molten droplets to form micronized particles comprising the poorly water soluble bioactive agent.

20. The process of claim 19, wherein step (a) comprises a superheated aqueous phase heated to a temperature ranging from the melting point of the first poorly water soluble bioactive agent to less than the melting point of the second poorly water soluble bioactive agent.

* * * * *